United States Patent
Song

(10) Patent No.: US 12,207,625 B2
(45) Date of Patent: *Jan. 28, 2025

(54) RUMINANT ANIMAL MONITORING SYSTEM

(71) Applicant: LELY PATENT N.V., Maassluis (NL)

(72) Inventor: Xiangyu Song, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/231,388

(22) Filed: Aug. 8, 2023

(65) Prior Publication Data

US 2023/0380385 A1 Nov. 30, 2023

Related U.S. Application Data

(63) Continuation of application No. 17/606,220, filed as application No. PCT/NL2020/050281 on May 4, 2020, now Pat. No. 11,771,062.

(30) Foreign Application Priority Data

| May 10, 2019 | (NL) | ..................................... | 2023103 |
| Sep. 17, 2019 | (NL) | ..................................... | 2023839 |

(51) Int. Cl.
*A01K 29/00* (2006.01)
*G06T 7/70* (2017.01)
(Continued)

(52) U.S. Cl.
CPC .............. *A01K 29/005* (2013.01); *G06T 7/70* (2017.01); *G06V 20/35* (2022.01); *G06V 20/52* (2022.01);
(Continued)

(58) Field of Classification Search
CPC .................... A01K 29/005; G06T 7/70; G06T 2207/10016; G06T 2207/10028;
(Continued)

(56) References Cited

U.S. PATENT DOCUMENTS

| 9,684,956 B2 | 6/2017 | Liao |
| 10,154,654 B2 | 12/2018 | Van Der Kamp |

(Continued)

FOREIGN PATENT DOCUMENTS

| CN | 109068613 A | 12/2018 |
| EP | 3 449 719 A1 | 3/2019 |

(Continued)

OTHER PUBLICATIONS

International Search Report issued on Sep. 30, 2020 in PCT/NL2020/050281 filed on May 4, 2020, 3 pages.

(Continued)

*Primary Examiner* — Tom Y Lu
(74) *Attorney, Agent, or Firm* — Oblon, McClelland, Maier & Neustadt, L.L.P.

(57) ABSTRACT

There is provided a system and method for automatically monitoring a ruminant animal. The system comprises a 3D camera system that obtains images from a region of interest, in particular the paralumbar fossa. An image processor determines the surface curvature in the region of interest, as a function of time. Based on the frequency with which this function attains local maxima, a health indication for the animal is generated.

21 Claims, 2 Drawing Sheets

(51) Int. Cl.
*G06V 20/00* (2022.01)
*G06V 20/52* (2022.01)

(52) U.S. Cl.
CPC ............... *G06T 2207/10016* (2013.01); *G06T 2207/10028* (2013.01)

(58) Field of Classification Search
CPC ...... G06T 7/0016; G06V 20/35; G06V 20/52; A61B 2503/40; A61B 5/1079; A61B 5/4238; A61B 5/1077; A61B 5/7235; A61B 5/7257; A61B 5/746
See application file for complete search history.

(56) References Cited

U.S. PATENT DOCUMENTS

| | | | |
|---|---|---|---|
| 10,244,736 B2 | 4/2019 | Song | |
| 10,816,387 B2 | 10/2020 | Fournier | |
| 10,932,450 B2 | 3/2021 | Tippery | |
| 11,154,032 B2 | 10/2021 | Brayer | |
| 11,771,062 B2 * | 10/2023 | Song | G06V 20/35 382/110 |
| 2014/0180130 A1 | 6/2014 | Granz et al. | |
| 2015/0265187 A1 | 9/2015 | Bernal et al. | |
| 2018/0228587 A1 | 8/2018 | De Groot et al. | |
| 2019/0150405 A1 | 5/2019 | Yagi et al. | |

FOREIGN PATENT DOCUMENTS

| | | |
|---|---|---|
| WO | WO 2012/138290 A1 | 10/2012 |
| WO | WO 2015/030611 A1 | 3/2015 |
| WO | WO 2018/065957 A1 | 4/2018 |

OTHER PUBLICATIONS

Burfeind, 0. et al., "Technical note: Evaluation of a scoring system for rumen fill in dairy cows," J. Dairy Sci., vol. 93, No. 8, 2010, pp. 3635-3640, XP055411413.

* cited by examiner

RUMINANT ANIMAL MONITORING SYSTEM

This application is a continuation of U.S. Ser. No. 17/606,220, filed Oct. 25, 2021, and issued as U.S. Pat. No. 11,771,062, which is a 371 of PCTNL2020/050281 filed May 4, 2020 and claims benefit of NL Application No. 2023839, filed Sep. 17, 2019 and NL Application No. 2023103, filed May 10, 2019. The contents of each of these applications are incorporated herein by reference in their entirety.

FIELD

The present invention relates to a system for automatically monitoring a ruminant animal, in particular a dairy animal such as a cow, comprising a 3D camera system for obtaining a plurality of 3D images of at least a region of interest of the animal at consecutive points in time during at least a predetermined period of time, a control device connected to the 3D camera system, the control device being provided with an image processing device for processing the obtained plurality of 3D images, and an output device.

BACKGROUND

Such animal monitoring systems are known. E.g. document WO12/138290A1 discloses a system for determining a gut fill level of the rumen of a dairy animal. A 3D camera system determines the depth or the volume of the rumen triangle. Also known are 3D camera-based body condition scoring systems.

However, a gut fill level or body condition score is only of limited importance for the health status of a ruminant animal.

Thus, there is a need for a practical, simple and reliable system and method for determining more and/or better health indication information about a ruminant animal based on 3D images of the animal.

SUMMARY

The present invention achieves this goal at least partly, and in one aspect provides a system for automatically monitoring a ruminant animal, in particular a dairy animal such as a cow, comprising a 3D camera system for obtaining a plurality of 3D images of at least a region of interest of the animal at consecutive points in time during at least a predetermined period of time, a control device connected to the 3D camera system, the control device being provided with an image processing device for processing the obtained plurality of 3D images, and an output device, the control device being arranged to determine a health indication on the basis of the processed images, and to output the health indication to the output device, wherein the image processing device is arranged to determine a region of interest in the plurality of 3D images and one of calculate for each 3D image a curvature value of the region of interest, and determine the calculated curvature as a function of time, or measure for each 3D image a relative position of at least predetermined point of said region of interest with respect to the animal, and determine said relative position as a function of time, wherein the control device is arranged to determine points in time when local extreme values of the function of time occur, and the health indication by analysing the points in time with respect to a predetermined criterion.

Use herein is made of the insight that knowledge of the reticuloruminal motility may provide valuable health information. The reticulorumen performs digestive functions a.o. by cyclically contracting and relaxing. Herein, primary contractions start from the reticulum and pass across the rumen. These contractions mix and circulate the digesta. These contractions may be observed by means of a 3D camera. Note herein that determining only a single value of the curvature, such as might be derivable from the prior art systems that determine a depth or volume of the rumen area, or a body condition score, from a single image, would not lead to any information regarding contractions.

It is noted that rumen motility is sometimes determined by a veterinarian, by auscultation (listening to bodily sounds) and palpitating (examining by feeling the body). This requires the presence of a veterinarian, which is impractical for continuous monitoring. Thus, in practice it is only used if there is a suspicion of some health problem anyway. Thus, the chance of determining health problems or a precursor thereto, at a very early stage, is hereby excluded. In addition, practical tests have shown that human observation of the contractions in a well-filled rumen is more difficult than can be achieved with the system according to the present invention, which thus gives advantages in terms of reliability. Veterinarian's motility determination can also lead to errors and subjectivity, because of human assessment. But it also leads to stress or other disturbance for the animal or herd. This in itself may be a cause for deviations in the true reticuloruminal motility, so that the veterinarian might be led to an incorrect assessment due to stress or the like that is caused by his own assessing. For these reasons, it is desirable to have a non-contact system for determining a health indication, as is offered by the present invention.

In the method, the local extreme values of the function may be determined as, in particular, local maxima in time, of the calculated curvature value or the relative position. A maximum in position is here taken to be a position closest to the 3D camera. "Local" is considered in the mathematical sense of "with respect to the variable", not necessarily with respect to position in space.

The images are obtained at consecutive points in time. These points in time need not be distributed at regular intervals in time, but they need to be known in order to allow a temporal analysis of the images. Furthermore, the images should also be obtained during at least a predetermined period of time, again in order to allow a reasonable temporal analysis. The timeframe depends on the expected recurrence intervals, that may depend on the type of animal etc. In practice, it is preferred if the images are obtained during at least 2 minutes, and more preferably during at least 5 minutes. At least for cows, this allows to observe a sufficient number of contractions for a reliable determination of a health indicator.

The 3D camera may be immobile or may be moveable, as long as it is arranged to observe the region of interest. Thereto, it could be provided with a lens with such a field of view that the region of interest will be comprised in the image for all likely positions of the animal with respect to the 3D camera, taking into account that the animal may move during obtention of the images. In particular, the 3D camera may be arranged to be directable to the region of interest, by means of a provided mover control, connected to the control device. The control device may then be able to actively direct the 3D camera to the region of interest, for example based on the image processing. It is then possible to use a smaller field-of-view, which in turn allows a higher accuracy.

In fact, determining a region of interest in the plurality of 3D images may advantageously benefit from some form of tracking, especially when the animal moves. For example, the image processing device is arranged to recognise a particular point in the image, and use that point to track and position the consecutive images for comparison. Based on such tracking, a camera's mover control may be arranged to position the 3D camera such that the recognised point is always in the same position in the image.

DETAILED DESCRIPTION

Other special and inventive embodiments are described in the dependent claims, as well as in the now following part of the description.

In embodiments, the 3D camera system comprises a time-of-flight camera or a structured-light camera. Such types of 3D camera provide a relatively high framerate of up to 30 Hz or more. This ensures that contractions or other movements of the region of interest will not be missed between images, while animal movements may easily be accounted for in the obtained 3D images. However, it is not necessary to have such high frame rates, which lead to a relatively high number of calculations. Other 3D camera types, such as stereo cameras, or laser scanners are also possible. Examples of preferred 3D camera are the "SwissRanger" 3D cameras or equivalents, and "Kinect" type camera devices. In all this, the property of the camera to provide 3D information is put to use in the invention to provide curvature data of the animal's region of interest.

In embodiments, the region of interest is a left paralumbar fossa, also called the rumen triangle. This is the more or less triangular region on the left side of the ruminant animal, that provides a relatively clear view of the reticulorumen. It is easily recognisable automatically, e.g. by means of template matching, using a triangle, and matching regions of relatively high local curvature. A comparable method is described in https://nl.mathworks.com/help/images/ref/normxcorr2.htm and reference is made to this source for mathematical details. In particular the region of interest is a partial region within said left paralumbar fossa, i.e. not the whole rumen triangle but only a smaller or larger part of it. It was found that the useful information may also be collected by looking at a part of the paralumbar fossa, which limits the number of determinations and calculations.

In embodiments the curvature value comprises or is an average value of the curvature value of the region of interest, in particular averaged over a plurality of points across the region of interest. The curvature value may be determined according to any desired method, as long as it is an indication of the degree of curvedness of the surface. This value may, according to this embodiment, be determined by analysing the complete or partial region of interest. It is also possible to analyse a plurality of points in said complete or partial region, again as long as a good indication of the degree of curvedness is obtained. In addition, it is noted that the sign of the curvature value should not be ignored, in that a convex region of interest should give a positive value and a concave region of interest a negative value, or vice versa, as long as the two are different. This prevents meaningless double peaks if the region of interest should vary in appearance between convex and concave.

A useful example of calculating curvature of the surface (region of interest) is by Principal Component Analysis of a covariance matrix with neighbours for points on the surface. This gives three eigenvalues $\lambda 0$, $\lambda 1$, $\lambda 2$ for the matrix, and the curvature $\sigma$ for a point may be estimated by $\sigma = \lambda 0/(\lambda 0 + \lambda 1 + \lambda 2)$, with $\lambda 0$ is the smallest eigenvalue. The surface curvature may then be determined by averaging (or adding, etc.) the surface curvature for a number of points, such as a matrix of points, in the region of interest. It turns out that a grid or lattice of surface points around some fixed and easily recognisable point in the region of interest suffices, as already stated above. The fixed point could e.g. be the surface point used for tracking, with the highest cross-correlation coefficient. Yet this is not to exclude other ways of estimating surface curvature, such as by calculating the variation of all the surface normal vectors in the region of interest, or the part/window thereof.

After determining the surface curvature, which can be done for each image, the result is a curvature that is a function of time. In analysing this function, local extremes, in particular local maxima, are determined. Herein, it is advantageous to consider a value a local extreme if it is the highest in a window of a predetermined time before and after that value's time, such as a few seconds, say 3 s. This prevents noise spikes etc. from interfering too much.

In embodiments, the control device is arranged to determine a frequency of the local extremes, in particular local maxima, in time, and to analyse the points in time by comparing the determined frequency with a predetermined frequency criterion. The extremes, in particular the maxima, will occur with some more or less regular frequency. By determining this frequency, or frequency band, valuable information about the health of the animal may be obtained, and a health indication given.

In embodiments, the control device is arranged to filter the function in time of the calculated curvature by filtering out temporal variations in said function that have a frequency outside a predetermined frequency range. With this measure, irrelevant changes, such as those caused by animal movements/displacements or noise, may effectively be removed. Herein, use is made of the insight that the relevant contractions occur within an animal specific frequency band. In particular, but non-limiting embodiments, the control device is arranged to perform a Fourier transformation of the calculated curvature function to construct a transformed frequency function, then to remove all parts of the transformed frequency function outside the predetermined frequency range to obtain a clean frequency function, and determine a contraction frequency by analysing the clean frequency function. Fourier transforms are a well-known and effective way of removing frequency components from a temporal signal. Yet, other ways of filtering may be applied, such as bandpass filters, that achieve a similar effect. The analysing of the clean frequency function may be done by determining the frequency value with the strongest signal value, or the average of the frequency signals within the remaining signals in the clean frequency function, or any other analysis that gives a frequency value indicative of the contraction frequency. In addition, but only optionally, the control device may be arranged to perform an inverse Fourier transformation on the clean frequency function, to obtain a clean curvature function. This clean curvature function may be displayed for visual checking.

In particular, the predetermined frequency range is or comprises the frequencies from 0.5-4 per minute, inclusive. For cows, this turns out to be a useful frequency band, outside of which no signals represent meaningful contractions. For other species a different frequency band might be applicable.

In embodiments, said frequency criterion comprises generating a health warning when the determined frequency is lower than a predetermined frequency threshold. It is found that for normal animals, the frequency with which reticuloruminal contractions occur has at least a certain value, and also that for animals suffering from clinical or even sub-clinical diseases, this frequency decreases. This allows to determine a health warning, such as an entry on an attention list, a message to a farmer or veterinarian, an audible or visible alarm, etc. All this serves to draw attention to a specific animal for further health checks, because it was found that some value was out of the ordinary for said animal.

In embodiments, said frequency threshold is a historical value for said animal, in particular a historical average for said animal, or said frequency threshold is a literature value for said animal, in particular in dependence of one or more of a breed, an age, a number of days in lactation, or a type of feed or feeding scheme, respectively, of said animal. This allows to finetune the frequency threshold to animal specifics, in order to prevent unnecessary health warnings. For example, when animals are fed mainly roughage, the contraction frequency is generally higher than when animals are fed a concentrates rich diet the threshold may then be adapted accordingly. It is remarked here that literature values may be a starting point, while processing historical values, optionally by means of deep learning and so on, may lead to threshold values with improved reliability.

In particular, the ruminant animal is one of a herd of ruminant animals, and said frequency threshold is dependent on an average frequency for said herd of ruminant animals, more in particular wherein said average is a momentary or running average. This ensures that variations that hold for all of the herd may be taken into account without causing an alarm (or health warning). If the herd is allowed to graze on a specific day, after staying and feeding indoors for months, such as in wintertime, there may be herd-wide changes in the reticuloruminal frequency that are normal. It would then not make sense to give an alarm for all animals. Yet, if for some animal this change is markedly different, there may still be given an alarm.

More generally, it holds that under practically all circumstances a change with respect to the herd average should give to an alarm, at least to investigate possible reasons for this deviation. In many cases, a deviation from the herd average frequency is a good indicator for a disease, such as in particular metabolic diseases.

For example, the frequency threshold may have a value that is an absolute or relative value below or below the herd average frequency, such as 0.5 Hz or 15% above or below the herd average frequency value. But depending on the type of animals, herd size, desired accuracy and so, other number may of course be chosen.

In embodiments, said frequency threshold is dependent on a type of activity being performed by the animal, such as feeding, being milked, or resting. Herein, use is made of the insight that the frequency of the contractions depends on the type of activity that the animal is momentarily involved in. For example, if the animal is eating, the frequency will often be higher, i.e. on the high side within the expected frequency band. Contrarily, in stress situations, or when resting, the frequency will be lower.

In embodiments, the system is arranged to determine a rumen fill level based on the obtained plurality of images, or at least an absolute or relative change therein. Basically, the same method may be applied as in the prior art document WO12/138290A1, the parts of which describe such method deemed incorporated. Briefly, the method and system disclosed therein determine an average concavity or convexity of the rumen triangle, and determine therefrom the rumen fill value. Note that in the present embodiments of the present invention it is possible and advantageous to use more than one of the images, in order to determine an average value of the curvature, and thus of the rumen fill. This ensures a correct determination of the true rumen fill value, that is not or hardly influenced by sudden movements, breathing, and so on.

By thus determining a rumen fill value, the system is able to determine even more accurately when a health warning or an alarm may be given. In particular, the control device is arranged to give a health warning if one of the following occurs:

the determined frequency decreases in time and the determined rumen fill value increases in time;

the determined frequency changes more after a change in regime than does the herd average frequency value;

after a regime change, the determined frequency for an animal does not return to the frequency for that animal before the feed regime change; or after a regime change, the determined frequency for an animal does return to its original value but more slowly than does the herd average value, by at least a predetermined amount.

The first of these four possibilities is a sign of inhibited rumen motility, which is a sign of metabolic disease, in particular ruminal acidosis, which should be treated.

The second to fourth possibilities relate to quantifying metabolic plasticity and adaptation to a regime change. Such a regime change is in particular a change in the feeding regime, but may also be a change in (stall) climate, herd density or any farm management practice. In each case, closer monitoring is advised because the indicated changes are a sign of metabolic problems. Herein, it is noted that determining or quantifying such metabolic plasticity has been done up to now by means of blood values and/or laboratory tests of milk. The present inventor has found that a similarly effective health warning system is available by means of the present systems and methods, which are non-invasive and thus less of a discomfort to the animals.

It is also possible to use the determined frequency and optionally the rumen fill value, as a check on other indicators. For example milk yield is often used as a health warning criterion. However, a drop in milk yield by itself need not indicate illness, and a health warning only based on milk yield may then lead too often to false-positive health warnings or warnings that come too late and cause a permanent decrease in health or production. By the present invention, a determined reticuloruminal contraction frequency that is too high or too low, either in an absolute sense or with respect to a herd average, or a determined frequency that goes down while the rumen fill value goes up, and so on according to the other combinations mentioned in the foregoing, may not only by themselves give rise to a health warning, but in fact also the other way around, i.e. if milk yield goes down and would normally lead to a health warning, this may be overruled by the control unit if the determined frequency remains stable. The control unit is then arranged to give a health warning or not accordingly. Similarly, if rumen fill and/or milk fat concentration decreases but the determined reticuloruminal contraction frequency of the animal remains stable, there is no need for a health warning, and the control unit should be arranged accordingly. However, a feed warning may be given, since the latter situation relates to insufficient feeding (intake), rather than to an (acute) disease of the animal. In all cases, the system should comprise any means known in the art for determining the additional quantity, such as milk yield or milk fat concentration.

Summarisingly, the invention provides an advantageous method for monitoring ruminant health, comprising automatically determining reticuloruminal contraction frequency and rumen fill by means of the system according to the present invention, and generating a health warning based on a comparison of the determined reticuloruminal contraction frequency and the determined rumen fill with a predetermined frequency value, a predetermined rumen fill value, respectively. Herein, the respective predetermined value may be a time averaged or herd averaged value, a literature value and so on. A big advantage of this method is that basing the health warning on these parameters speeds up the detection of serious issues, since when there is some metabolics related issue, rumen contractions and rumen fill change first, and only later is this followed by changes in body condition score, milk production and milk quality. The description will now continue with further system embodiments.

In embodiments, the system comprises at least one station, each station selected from the group of milking stations, feeding stations, drinking stations, treatment stations, separating stations and selection stations, wherein the 3D camera system comprises a 3D camera provided in at least one of said stations. Such stations are well-suited for placing the 3D camera system, for the animal will be in one position for a relatively long time. In particular a milking station is well suited, because it may even be predicted for how long the animal will remain there, based on expected milk yield and other historical data. On average, the animal will be present in the milking station for at least 5 minutes, which provides a very suitable time window for determining the frequency as already stated above. But also at other stations such measurements with the 3D camera system are possible. Even when not every instance leads to reliable measurements, for example because the animal stays in a suitable position for a too short time, the system of the invention allows to monitor the animal at many instances, so that a good insight in its health may be obtained, and a warning can be given early in case something is wrong. It is remarked here that at each station, besides the measuring of reticuloruminal contractions, some other action may be performed, such as milking, feeding, treating or separating the animal. Advantageously, a separating station is coupled to a milking station or feeding station, such that in case a health warning is given for a particular animal in the station, the control device may send the animal to the separating station for it to await a health check by the farmer or veterinarian.

In embodiments, the control device is arranged to determine time intervals between the local extremes based on the determined points in time, and to analyse the points in time by comparing the determined time intervals with a predetermined time interval criterion. In the above, the system uses a frequency based analysis to determine a health indication or warning. Yet, it is also possible to base the analysis on the time intervals between the local extreme values. In fact, this analysis would come down to the same as frequency based analysis after a transform from the time domain to the frequency domain. Yet, in some cases it may be simpler to just analyse the various time intervals, such as by determining an average time interval between local maxima. Such average time interval should then be within a time interval range, that may be animal dependent, activity dependent and so on. All features relating to special embodiments in the frequency dependent analysis system also apply for the time interval based analysis system.

In a second aspect, the present invention relates to a method of determining a health indication for an ruminant animal, in particular a cow, which method uses a system according to the first aspect of the invention and comprises the steps of obtaining a plurality of 3D images of at least a region of interest of the animal at consecutive points in time during at least a predetermined period of time, processing the obtained plurality of 3D images, determining a region of interest in the plurality of 3D images, one of calculating for each 3D image a curvature value of the region of interest, and determining the calculated curvature as a function of time, or measuring for each 3D image a relative position of at least predetermined point of said region of interest with respect to the animal, and determining said relative position as a function of time, and determining points in time when local extreme values of the function of time occur, and the health indication by analysing the points in time with respect to a predetermined criterion, and/or an amplitude of said function, and the health indication by analysing the determined amplitude with respect to a predetermined amplitude criterion. Since this is the method counterpart of the system aspect of the invention, it suffices to state here that all special features and advantages mentioned for measures relating to special embodiments of the system aspect of the invention apply as well for the method aspect.

It is stressed here that the present method is not a diagnostic method, although it could be used in a diagnostic method. After all, the method only helps in determining whether something could be wrong with an animal. It is not able to make a diagnosis as to what disease is present, if any, in an animal for which a health warning is given.

DESCRIPTION OF THE FIGURES

The invention will now be elucidated with reference to one or more exemplary and non-limiting embodiments, as well as to the drawing, in which.

DESCRIPTION OF PARTICULAR EMBODIMENTS

Figure 1:
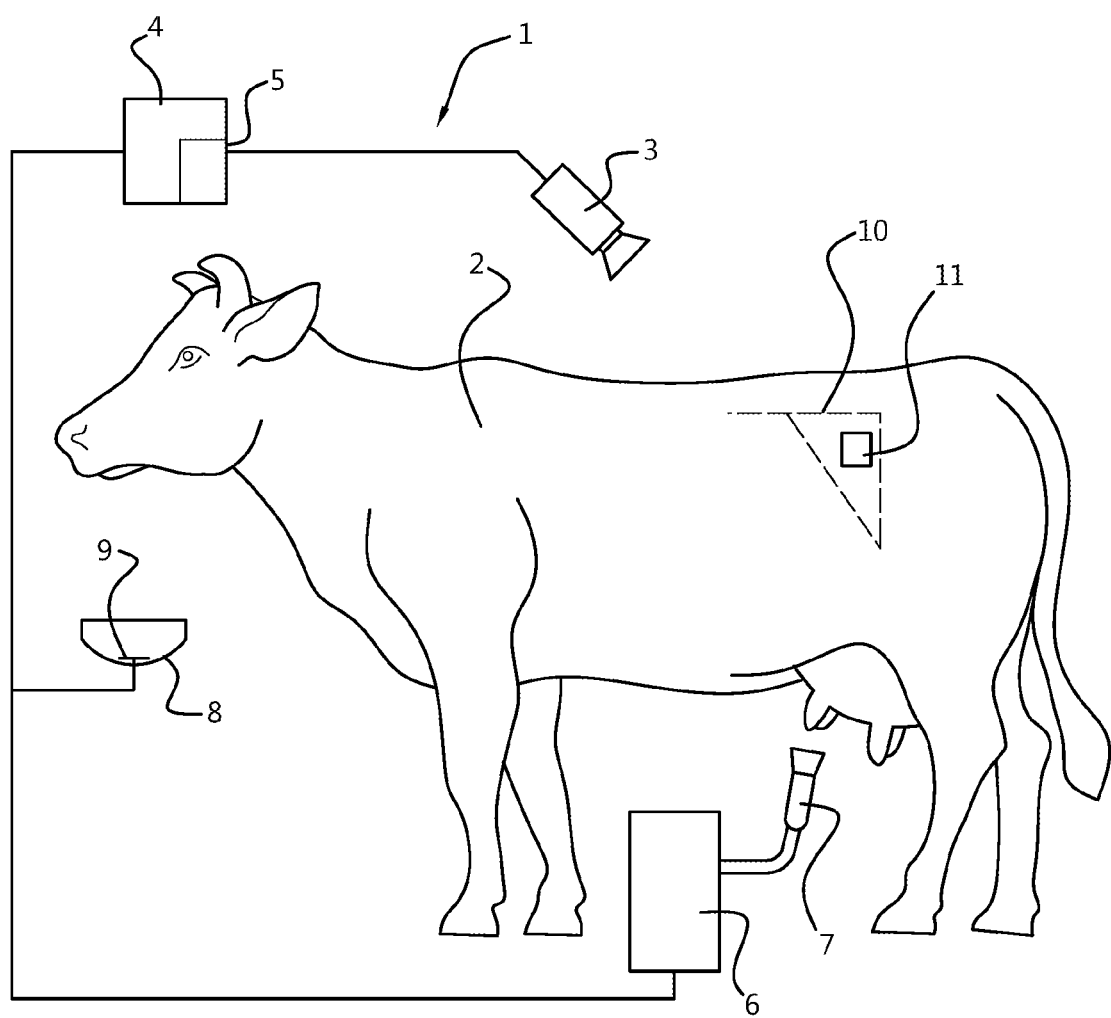
FIG. 1 very diagrammatically shows a system 1 according to the invention.

FIG. 1 very diagrammatically shows a system 1 according to the invention, for determining a health indication for a cow 2, and comprising a 3D camera 3, a control device 4 with an image processing device 5, a milking robot 6 with a teat cup 7, and a feeding trough 8 with a sensor 9. A region of interest in the form of the left paralumbar fossa is indicated with reference numeral 10, and a subregion or window with reference numeral 11.

In the embodiment shown, there is very diagrammatically shown a milking station, by way of a milking robot 6, that milks the cow 2 with teat cups 7, one of which is shown here. As soon as the milking process starts, i.e. after identifying the cow and deciding she will be milked, the control device 4 will be able to estimate roughly the time that the cow will spend at the milking station. For this, she may use a standard, minimum time, historical milking times for the cow, or even an estimated milking time based on production and milking interval, as is per se known in the art. For virtually every milking, this time will be at least 5 minutes, and often up to 8 or 9 minutes. In case the cow will not be milked, she will be urged outside, and there will not be sufficient time to perform meaningful measurements.

Alternatively, the station is a feeding station, indicated diagrammatically by the feeding trough 8, that has a sensor 9 that indicates the start of eating of the cow, by pressing with its snout. Most milking stations will also have a feeding trough, but it may be a stand-alone system. Yet other alternatives may be a drinking station (or ~trough), a treatment station and so on. Also, most stations will have animal identification (not shown here) with which the animal may be recognised and settings (milking, feeding, treatment) may be individually adjusted. Furthermore, it is also possible to trigger the 3D camera system by means of this animal recognition, for example if the system should monitor only specific animals.

When the 3D camera is turned on, it begins to image the animal's region of interest (hereinafter: ROI, here indicated as the left paralumbar fossa, indicated by a dashed line. In order to be able to obtain sufficiently reliable data, the frame rate is at least one per second, but preferably at least ten times as high. In order to ensure that the ROI is in view of the camera during imaging, there may be provided a wide-angle lens on the camera, such that while the animal is at or in the (milking, feeding, . . . ) station, the ROI will be in view. It is also possible to provide a motor to move the camera, based on recognition of the ROI in the image by the image processing device 5. Tracking the ROI in this way is in itself a known technology. The advantage hereof is that the ROI may form a larger part of the image, and may thus be imaged with higher resolution.

The obtained 3D images are processed by the image processing device 5, as will be elucidated further below. The result of the processing is a curvature value for the ROI as a function of time. This function is analysed by the control device 5, and one or more criteria are applied to determine a health indication for the cow 2. In case the health indication gives rise to an alarm or the like, the control device 4 may enter the cow 2 on an attention list, issue an audible or visible alarm, separate the cow 2 after the station 2, 6, or the like. Then, the cow 2 will be examined further, by the farmer or veterinarian.

In use of the system, and in the method, the obtained 3D images form a 3D representation of the ROI. In order to limit the number of calculations, to be described below, it is possible to limit the ROI to only a part of the left paralumbar fossa, such as to the subregion or window 11 in the present example, although this is not necessary.

Instead of determining a depth or volume of this ROI, as is done in prior art systems in order to determine rumen fill, the present invention determines a changing curvature value of the ROI. This is based on the insight that natural processes influence the rumen shape, such that the predictive value of a momentary rumen fill value seems limited, but, contrarily, the predictive value of the analysis of the temporal changes in the curvature of the rumen, or left paralumbar fossa, region seem meaningful.

For each obtained 3D image, the (sub)region of interest is tracked by image processing, such as by recognising the top left corner of the left paralumbar fossa, and repositioning/resizing the image. And then a curvature value is calculated. This may be done in many ways, as long as it expresses the degree of curvedness of the ROI in a systematic way. One example will now be elaborated briefly.

The determination of the curvature will be limited to the subregion 11. For this subregion 11, the curvature value is determined as follows.

First, a covariance matrix is calculated from the nearest neighbors of the point.

$$C = \frac{1}{k}\sum_{i=1}^{k}(p_i - \bar{p})\cdot(p_i - \bar{p})^T$$

where k is the number of neighboring points, $p_i$ is the position vector of the i th neighboring point and $\bar{p}_i$ is the position vector of the centroid of the neighboring points. The resulting covariance matrix C will be a 3 by 3 matrix with 3 eigenvalues. The surface curvature σ can be estimated by the following equation $$\sigma = \frac{\lambda_0}{\lambda_0 + \lambda_1 + \lambda_2}$$

where $\lambda_0$, $\lambda_1$, $\lambda_2$ are the eigenvalues of covariance matrix C, with $\lambda_0$ the smallest eigenvalue.

Figure 2:
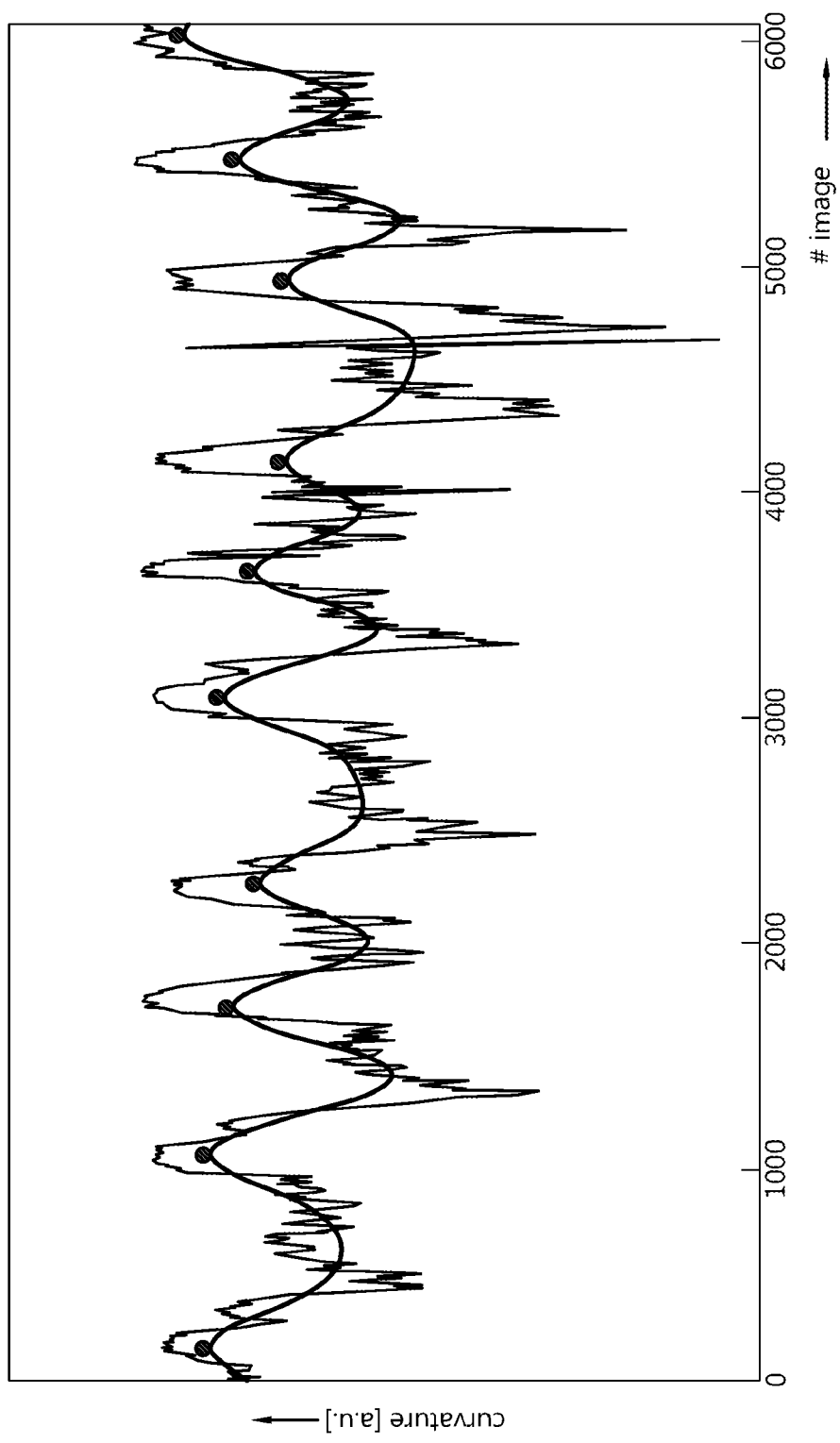
FIG. 2 shows an exemplary plot of the raw curvature versus time, and the smoothed curvature versus time function.

The resulting curvature value a may then be plotted as a function of time. This is done in exemplary FIG. 2, as the somewhat wildly varying curve. Note that the x-axis denotes image number, with in this case a frame rate of 30 Hz, or 1800 images/minute. Clearly, although a rough "beat" is discernible in the curve, it is difficult to extract meaningful information from this. However, it was realised that various sources of noise may be efficiently eliminated. For one, animal movements may be removed, as well as varying lighting conditions, which are in principle one-off variations and not regular variations. In addition, it may be possible to eliminate regular movements that are much faster than the expected contraction frequency, such as breathing. The latter is normally between about 25 and 50 breaths per minute, which is an order of magnitude higher than the reticuloruminal contractions. In this case, the above "noise signals" are removed by means of decomposing the signal by signal frequency, with the "pass" frequency range between 0.5 and 4.0 contractions per minute, and discarding the rest. Thereto, a Fourier transform of the signal was constructed, the pass-frequency range applied with cut-offs below and above the range, and the inverse Fourier transform was constructed, to regenerate a curvature-time function. This function is also plotted in FIG. 2, as the smooth curve. In the smooth curve, more or less evenly spaced peaks are clearly visible, and they also clearly have a frequency in the expected range. Note that this smoothed curvature function only serves for visual checks, while the Fourier transformed function serves as the basis for calculations and monitoring.

In the smoothed curve, the peaks, or maxima, have been indicated with a dot. The average frequency, thus for the reticuloruminal contractions, is about 9/(5800/1800)=2.8 contractions per minute. This is a normal frequency for the tested cows, in this case primiparous healthy Holstein and Swiss-Brown cows, so for this particular cow, a "healthy" indication may be given, and no health alarm need be given.

However, it is possible that a particular cow usually has a higher or lower value, based on historical measurements. In such a case, an health indication "still healthy, but check" may be given, i.e. some examination may be performed, but not very urgent, or the cow could be monitored more closely. It is also possible that the calculated contraction frequency is actually lower than a predetermined threshold value, such as when the determined frequency is between about 1 and 2 per minute during feeding. Such a value is not uncommon during resting, but should normally be higher during feeding. Therefore, in such a case the health indication "check urgently" may be issued by the control device, or an alarm sounded etc.

In the example shown, there is provided a 3D camera system in a milking station. The animal will be milked in the station a few times per day, such as 2-4 times/day. It is advantageous if the animal is monitored more often, because e.g. the measurement could fail, due to a too short time to conclude to meaningful information, or because of too violent movements or the like. Therefore, it is advantageous if the 3D camera system comprises one or more additional cameras in other positions, such as feeding stations, watering stations, or even cubicles or "resting stations". Note that the determined frequency may be compared with a correspondingly adapted threshold frequency, such as a lower threshold frequency when in a cubicle.

It is noted that the 3D camera generates 3D images, which represent a 2D image of the animal combined with, for each pixel, information about the distance to the camera. In the above embodiment, the curvature was calculated in a region of interest, and conclusions were drawn based on a time analysis of the curvature. It is also possible that the control device, with the image processing device, calculates the distance between a specific point in the region of interest and the camera. This point will also move towards the camera and back again, with the same frequency as the curvature changes. In other words, the relative position of the point with respect to the camera changes, with the same relevant frequency. Thus the present invention, both system and method, also function when they (are arranged to) measure the relative position of a fixed point in the region of interest (left paralumbar fossa or subregion thereof), and analyse the extremes, in particular the points in time when the fixed point is closest to the camera.

It is advantageous when this fixed point is determined with a sufficient precision and accuracy, in order to prevent artefacts or simply mismeasurements. Thereto, it is advantageous if the fixed point is easily recognisable in the image. Herein, it is helpful to determine the boundaries of the paralumbar fossa, which is a relatively easily recognisable triangle on the left side of the animal. The fixed point may then be determined by the image processing software to be in a relative position to the boundaries of the thus determined region of interest, such as in the geometric centre, or any other position. It is then relatively straightforward, even when performing the analysis afterwards instead of in real time, to determine a basic position of the animal by using the relative positions of the boundaries of the region (such as the ribs and the backbone, additionally indicating that it is advantageous to determine breathing rate, in order to subtract the corresponding signal). Movements of these boundaries as a whole count as displacements of the animal as a whole and are meaningless as to the contractions. After subtracting these, or otherwise accounting therefor, the true relative movement of the fixed point may be determined, and the rest of the analysis may more or less be copied for that relative movement.

The above described embodiments only serve to help explain the invention without limiting this in any way. The scope of the invention is rather determined by the appended claims.

The invention claimed is:

1. A system for automatically monitoring a ruminant animal, comprising:

a 3D camera system for obtaining a plurality of 3D images of at least a region of interest of the animal at consecutive points in time during at least a predetermined period of time, and
a control device connected to the 3D camera system, the control device being provided with
an image processing device for processing the obtained plurality of 3D images, and
an output device,
the control device being arranged to determine a health indication on the basis of the processed plurality of 3D images, and to output the health indication to the output device,
wherein the image processing device is arranged to determine a region of interest in the plurality of 3D images and one of:
calculate for each 3D image a curvature value of the region of interest, and determine the calculated curvature value as a function of time, or
measure for each 3D image a relative position of at least one predetermined point of said region of interest with respect to the animal, and determine said relative position as a function of time,
wherein the control device is arranged to determine:
points in time when local extreme values of the function of time occur, and
the health indication by analysing the points in time with respect to a predetermined criterion.

2. The system according to claim 1, wherein the 3D camera system comprises a time-of-flight camera or a structured-light camera.

3. The system according to claim 1, wherein the region of interest is a left paralumbar fossa, in particular a partial region within said left paralumbar fossa.

4. The system according to claim 1, wherein the curvature value comprises or is an average value of the curvature value of the region of interest.

5. The system according to claim 1, wherein the control device is arranged to determine a frequency of the local extremes in time, and to analyse the points in time by comparing the determined frequency with a predetermined frequency criterion.

6. The system according to claim 5, wherein the control device is arranged to filter the function in time of the calculated curvature by filtering out temporal variations in said function that have a frequency outside a predetermined frequency range.

7. The system according to claim 6, wherein the predetermined frequency range is or comprises the frequencies from 0.5-4 per minute, inclusive.

8. The system according to claim 5, wherein said frequency criterion comprises generating a health warning when the determined frequency is lower than a predetermined frequency threshold.

9. The system according to claim 8, wherein said frequency threshold is a historical value for said animal or wherein said frequency threshold is a literature value for said animal.

10. The system according to claim 8, wherein said frequency threshold is dependent on a type of activity being performed by the animal.

11. The system according to claim 1, comprising at least one station, each station selected from the group consisting of milking stations, feeding stations, drinking stations, treatment stations, separating stations and selection stations,
wherein the 3D camera system comprises a 3D camera provided in at least one of said stations.

12. The system according to claim 1, wherein the control device is arranged to determine time intervals between the local extremes based on the determined points in time, and to analyse the points in time by comparing the determined time intervals with a predetermined time interval criterion.

13. A method of determining the health indication for the ruminant animal which method uses the system according to claim 1, comprising:
obtaining a plurality of 3D images of at least the region of interest of the animal at consecutive points in time during at least a predetermined period of time,
processing the obtained plurality of 3D images,
determining the region of interest in the plurality of 3D images,
one of:
calculating for each 3D image the curvature value of the region of interest, and determining the calculated curvature as a function of time, or
measuring for each 3D image a relative position of at least a predetermined point of said region of interest with respect to the animal, and determining said relative position as a function of time,
and determining:
points in time when local extreme values of the function of time occur, and
the health indication by analysing the points in time with respect to the predetermined criterion.

14. The system according to claim 1, wherein the control device is arranged to:
perform a Fourier transformation of the calculated curvature function to construct a transformed frequency function,
remove all parts of the transformed frequency function outside the predetermined frequency range to obtain a clean frequency function, and
determine a contraction frequency by analysing the clean frequency function by determining the frequency value with the strongest signal value, or the average of the frequency signals within the clean frequency function.

15. The system according to claim 9, wherein the literature value for said animal depends on one or more of a breed, an age, a number of days in lactation, or a type of feed or feeding scheme, of said animal.

16. The system according to claim 10, wherein the activity being performed by the animal is selected from the group consisting of feeding, being milked, or resting.

17. The system according to claim 13, wherein the ruminant animal is a cow.

18. The system according to claim 1, wherein the image processing device is arranged to calculate for each 3D image a curvature value of the region of interest, and determine the calculated curvature value as a function of time.

19. The system according to claim 1, wherein the image processing device is arranged to measure for each 3D image a relative position of at least one predetermined point of said region of interest with respect to the animal, and determine said relative position as a function of time.

20. The system according to claim 1, wherein the control device is configured to determine a reticuloruminal contraction frequency.

21. The system according to claim 1, wherein the health indication is rumen motility.

* * * * *